United States Patent [19]

Dickerhoff et al.

[11] Patent Number: 5,683,441
[45] Date of Patent: Nov. 4, 1997

[54] INFLATABLE BLANKET HAVING AIR FLOW DEFLECTOR

[75] Inventors: Scott D. Dickerhoff, Ballwin; Thomas F. Kappel, St. Louis, both of Mo.

[73] Assignee: Mallinckrodt Medical, Inc., St. Louis, Mo.

[21] Appl. No.: 710,958

[22] Filed: Sep. 24, 1996

Related U.S. Application Data

[63] Continuation of Ser. No. 280,021, Jul. 25, 1994, abandoned.

[51] Int. Cl.$^6$ ................................................ A61F 7/00
[52] U.S. Cl. ...................................... 607/107; 5/941
[58] Field of Search ............................... 5/423, 469, 482, 5/713, 655.3, 941; 297/180.3; 607/104, 107; 137/561 A; 239/553

[56] References Cited

U.S. PATENT DOCUMENTS

| | | |
|---|---|---|
| 630,565 | 8/1899 | Safran. |
| 1,291,191 | 1/1919 | Semple. |
| 1,590,522 | 6/1926 | Kalman. |
| 1,777,982 | 10/1930 | Popp. |
| 2,093,834 | 9/1937 | Gaugler. |
| 2,110,022 | 3/1938 | Kliesrath. |
| 2,122,964 | 7/1938 | Sweetland. |
| 2,235,966 | 3/1941 | Summers. |
| 2,512,559 | 6/1950 | Williams. |
| 2,601,189 | 6/1952 | Wales, Jr.. |
| 2,617,915 | 11/1952 | Blair. |
| 2,700,165 | 1/1955 | Talisman. |
| 2,706,988 | 4/1955 | Weber. |
| 2,791,168 | 5/1957 | Mauch. |
| 2,834,033 | 5/1958 | O'Brien ......................... 5/502 |
| 2,998,817 | 9/1961 | Armstrong. |
| 3,034,132 | 5/1962 | Landsberger et al.. |
| 3,307,554 | 3/1967 | Thornton et al.. |
| 3,308,850 | 3/1967 | Gill. |
| 3,610,251 | 10/1971 | Sanderson. |
| 3,674,034 | 7/1972 | Hardy. |
| 3,740,777 | 6/1973 | Dee. |
| 3,757,366 | 9/1973 | Sacher. |
| 3,844,339 | 10/1974 | Kranz ......................... 165/46 |
| 4,026,299 | 5/1977 | Sauder ......................... 128/400 |
| 4,094,357 | 6/1978 | Sgroi ......................... 5/284 |
| 4,398,535 | 8/1983 | Guibert ......................... 128/399 |
| 4,457,295 | 7/1984 | Roehr ......................... 128/204 |
| 4,572,188 | 2/1986 | Augustine et al. ......................... 128/380 |
| 4,653,131 | 3/1987 | Diehl ......................... 5/494 |
| 4,660,388 | 4/1987 | Greene, Jr. ......................... 5/485 |
| 4,777,802 | 10/1988 | Feher ......................... 5/482 |
| 4,807,644 | 2/1989 | Sandhaus ......................... 128/849 |
| 4,867,230 | 9/1989 | Voss ......................... 5/423 |
| 4,959,877 | 10/1990 | Covil ......................... 5/423 |
| 4,997,230 | 3/1991 | Spitalnick ......................... 5/423 |
| 5,022,110 | 6/1991 | Stroh. |
| 5,044,364 | 9/1991 | Crowther ......................... 128/400 |
| 5,097,548 | 3/1992 | Heck et al. ......................... 5/414 |
| 5,106,373 | 4/1992 | Augustine et al. ......................... 604/113 |
| 5,125,238 | 6/1992 | Ragan et al. ......................... 128/400 |
| 5,165,400 | 11/1992 | Berke ......................... 128/400 |

(List continued on next page.)

FOREIGN PATENT DOCUMENTS

| | | | |
|---|---|---|---|
| 1325484 | 12/1993 | Canada. | |
| 0311336 | 4/1989 | European Pat. Off.. | |
| 149244 | 11/1931 | Switzerland ......................... | 5/423 |
| 003216 | 8/1985 | WIPO ......................... | 607/104 |
| 94 03131 | 2/1994 | WIPO. | |
| 95 20371 | 8/1995 | WIPO. | |
| 95 35077 | 12/1995 | WIPO. | |

*Primary Examiner*—Alexander Grosz
*Attorney, Agent, or Firm*—Rothwell, Figg, Ernst & Kurz, P.C.

[57] ABSTRACT

The present invention relates to a blanket for use with forced air convection systems, wherein the blanket includes an airflow deflector internal to the blanket and located near the air inlet port of the blanket. By providing a blanket with an airflow deflector, better distribution of air within the confines of the blanket may be achieved, which helps to reduce and eliminate problems associated with hot and cold spots within the blanket.

6 Claims, 5 Drawing Sheets

U.S. PATENT DOCUMENTS

| | | | |
|---|---|---|---|
| 5,184,612 | 2/1993 | Augustine | 128/400 |
| 5,265,599 | 11/1993 | Stephenson et al. | 5/423 |
| 5,300,098 | 4/1994 | Philipot | 607/96 |
| 5,300,100 | 4/1994 | Hickle et al. | 607/107 |
| 5,300,101 | 4/1994 | Augustine et al. | 607/107 |
| 5,300,102 | 4/1994 | Augustine et al. | 607/107 |
| 5,304,213 | 4/1994 | Berke et al. | 607/107 |
| 5,304,217 | 4/1994 | Stephenson et al. | 607/114 |
| 5,318,568 | 6/1994 | Kaufmann et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/423 |
| 5,350,417 | 9/1994 | Augustine | 607/104 |
| 5,360,439 | 11/1994 | Dickerhoff et al. | 607/104 |
| 5,384,924 | 1/1995 | Dickerhoff et al. | 5/421 |
| 5,392,847 | 2/1995 | Stephenson | 607/104 |
| 5,405,370 | 4/1995 | Irani | 607/104 |
| 5,405,371 | 4/1995 | Augustine et al. | 607/107 |
| 5,408,712 | 4/1995 | Brun | 5/502 |
| 5,443,488 | 8/1995 | Namenye et al. | 607/104 |

INFLATABLE BLANKET HAVING AIR FLOW DEFLECTOR

This is a continuation of application Ser. No. 08/280,021 filed Jul. 25, 1994, now abandoned.

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling air flow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine et al, a forced air convection system which can supply either cool or warm air to a blanket is described. The blanket in Augustine et al comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

OBJECTIONS OF THE INVENTION

It is one object of the present invention to provide a blanket for a forced air convection system that allows for better distribution of air within the confines of the blanket.

SUMMARY OF THE INVENTION

The above objects and others are accomplished according to the present invention by providing a blanket having an airflow deflector internal to the blanket located near the air inlet for the blanket.

DETAILED DESCRIPTION OF THE INVENTION

Figure 1:
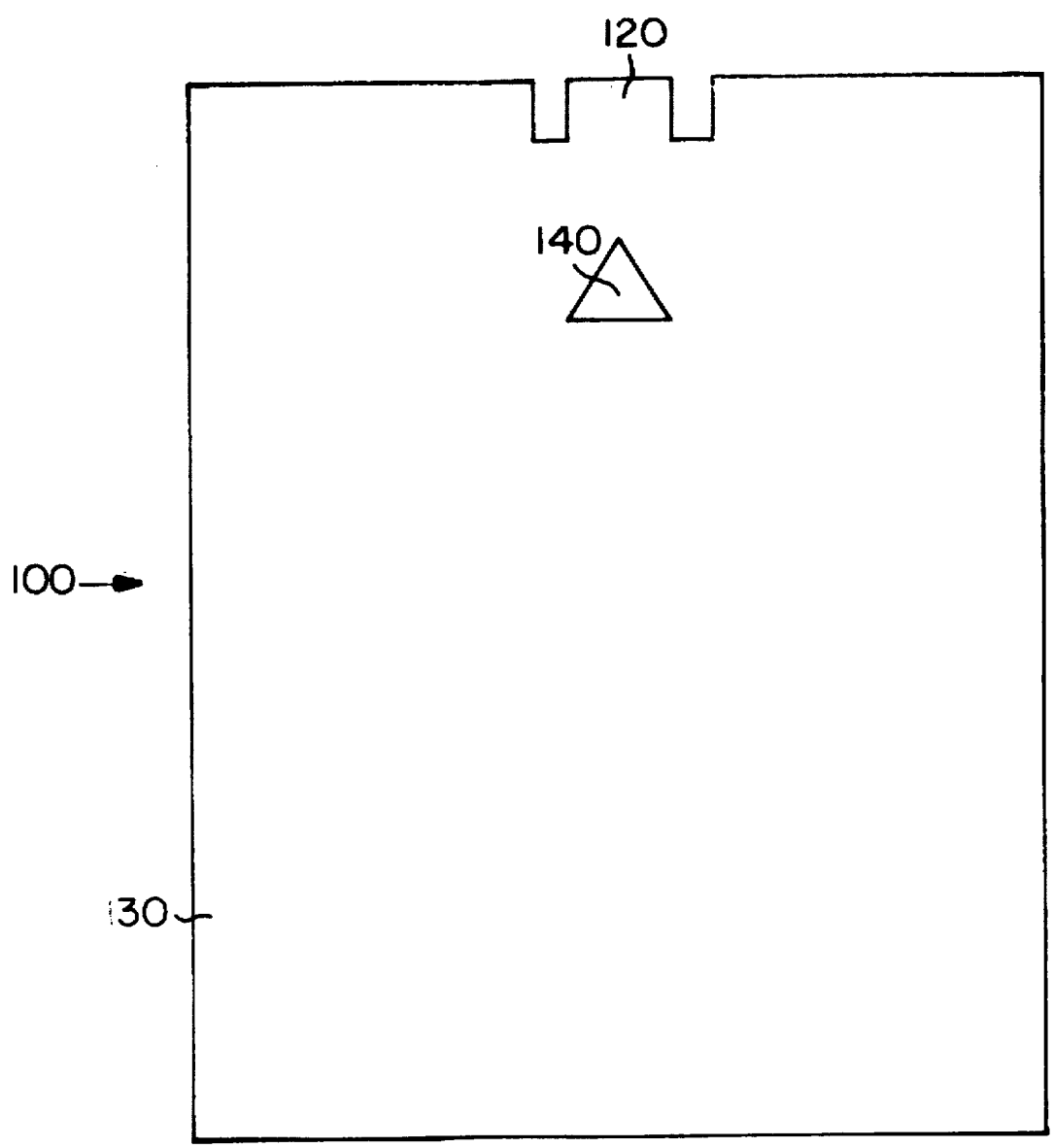
FIG. 1 is a plan view of the interior of a blanket for a forced air convection system according to one embodiment of the present invention.

FIG. 1 is a plan view of the interior of a blanket, generally, designated by reference numeral 100, for a forced air convection system. The blanket, 100, has a generally rectangular shape and includes an inlet port 120. The blanket 100, may be of any standard design, but preferably comprises two sheets of material which are sealed together along their peripheral edges and are connected together at connection spot welds discretely located in the interior surface portions of the sheets. By connecting the sheets of the blanket 100, in this manner, the blanket 100, may be inflated by supplying air to the interior area formed between the sheets of material. In FIG. 1, only the lower sheet 130, is shown.

The inlet port 120, communicates with the interior of the blanket 100, and may be used to supply air to the interior of the blanket 100, so as to inflate blanket 100. The lower sheet 130, of the blanket 100, may be provided with a plurality of small exit ports (not shown) to allow air to escape from the blanket 100, toward a patient.

In use, the blanket 100, may be placed over the body of a patient so that the inlet port 120, is oriented in a direction pointing toward the top of the head of the patient.

Figure 2:
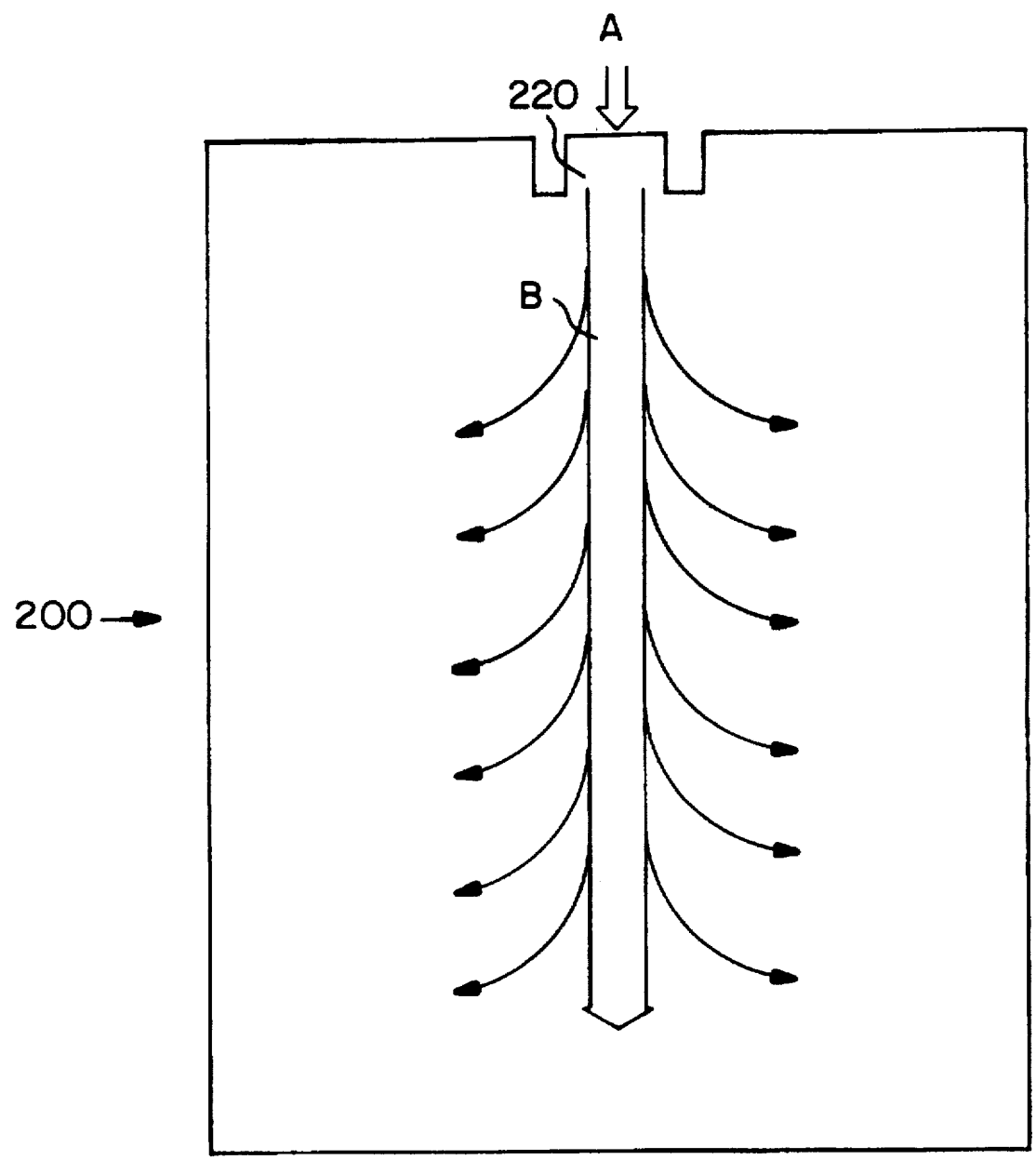
FIG. 2 is a schematic view of a prior art blanket showing the distribution of air entering the blanket.

One disadvantage associated with blankets for forced air systems is described in connection with FIG. 2. In particular, FIG. 2 shows a blanket, generally designated by reference numeral 200, having an air inlet port 220, through which air A, may be supplied from a suitable source. The branched path B, indicates how supplied air A, will tend to travel upon entering the blanket 200. As evident from FIG. 2, air A is supplied along path B, to most areas of the blanket 200, except for the corners nearest the inlet port 220. This can be very disadvantageous, especially in the case of supplying warm air to prevent hypothermia, as uneven heating may occur, creating "hot" and "cool" zones within the blanket 200.

Figure 3:
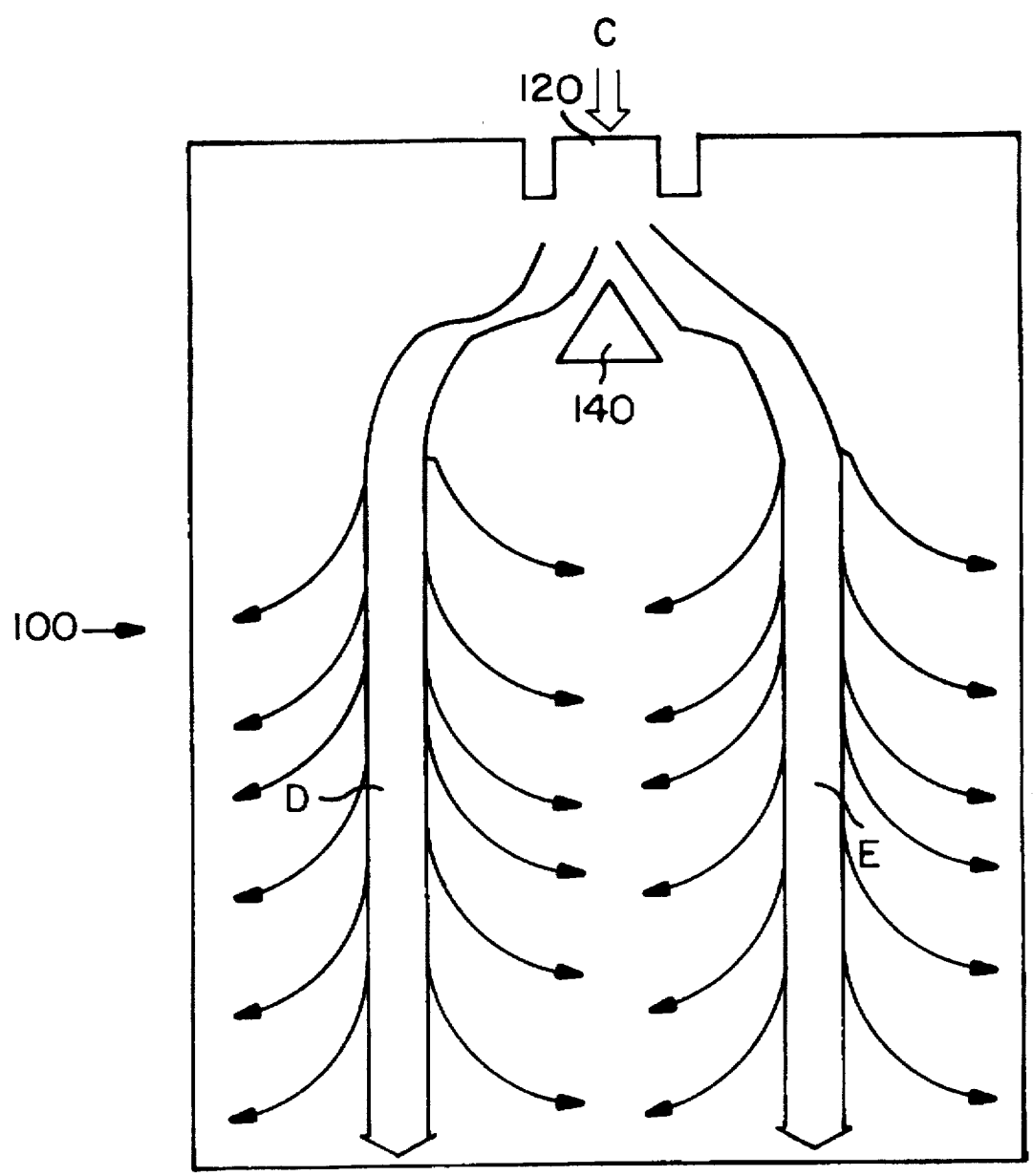
FIG. 3 is a schematic view of a blanket showing the distribution of air entering the blanket according to the present invention.

To overcome the disadvantages noted above, the blankets according to the present invention are provided with an airflow deflector interior to the blanket and near the inlet port. This is shown in FIG. 1, wherein blanket 100, includes an airflow deflector 140. As shown in FIG. 3, airflow deflector 140, acts to split a supplied air stream C, into two branched streams D and E, and provides more even distribution throughout the blanket 100, even to those corners nearest the inlet port 120.

While the above suggests placing blanket 100, so that the inlet port 120, is oriented toward the top of the patient's head, it will be recognized by one skilled in the art that the above discussion is just as applicable should the blanket 100, be placed with the inlet port 120, oriented toward the feet of the patient.

Figure 4:
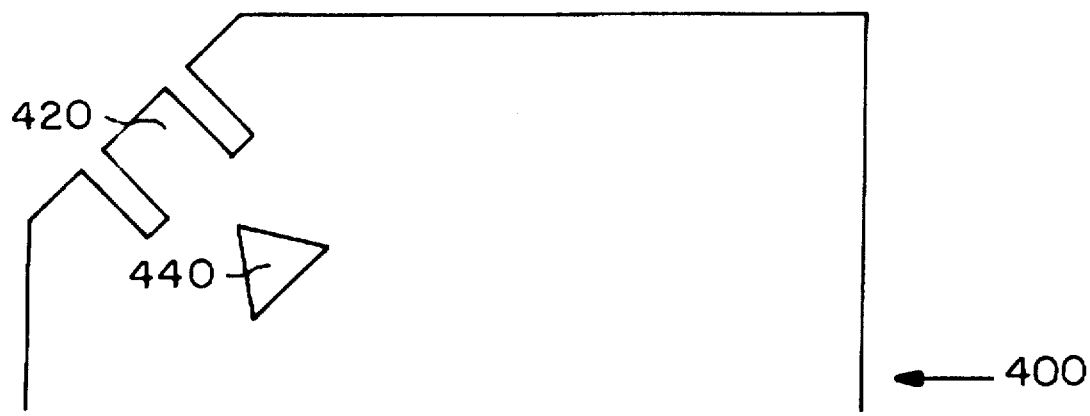
FIG. 4 is a plan view of the interior of a portion of a blanket according to the present invention according to another embodiment of the present invention.
Figure 5:
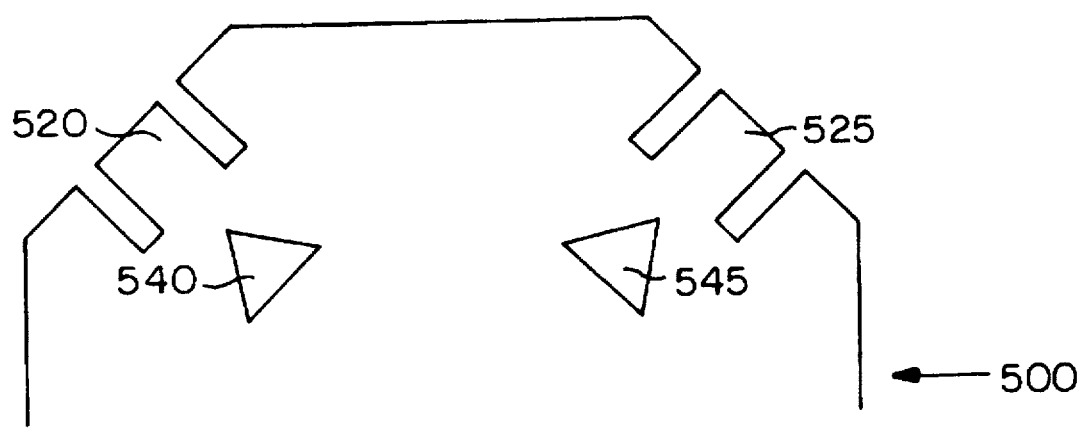
FIG. 5 is a plan view of the interior of a portion of a blanket according to the present invention according to a further embodiment of the present invention.
Figure 6:
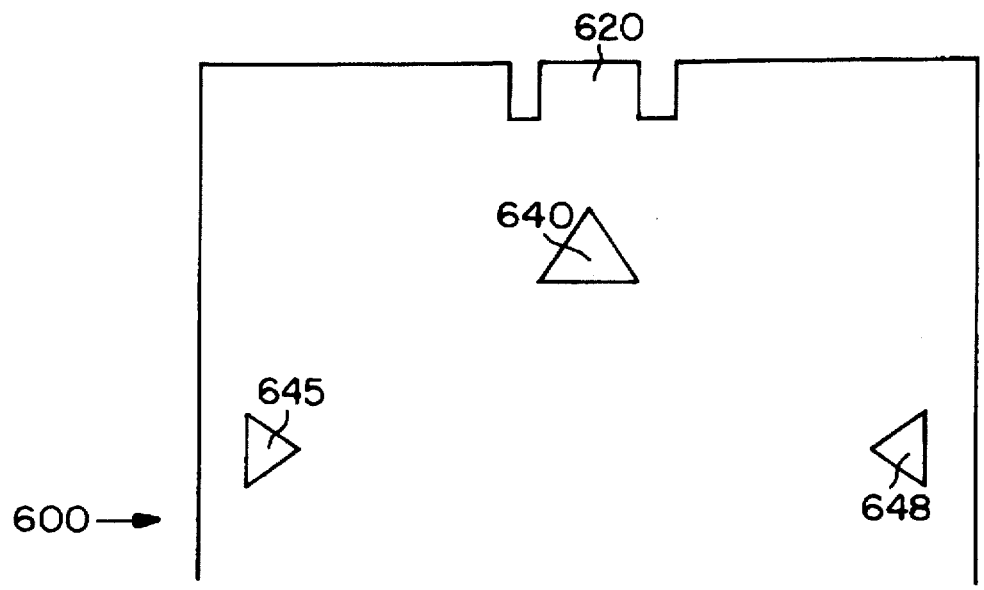
FIG. 6 is a plan view of the interior of a portion of a blanket according to the present invention according to a still further embodiment of the present invention.

FIGS. 4, 5 and 6 are each plan views of the interior of the portion of a blanket according to the present invention including the inlet port or ports, and showing various arrangements of the inlet ports and airflow deflectors associated therewith.

In particular, FIG. 4 shows a blanket, generally designated by reference numeral 400, having an inlet port 420, located at a corner of the blanket 400. An air flow deflector 440, is provided near the inlet port 420, to aid in the even distribution of supplied air within the blanket 400.

FIG. 5 shows a blanket, generally designated by reference numeral 500, having dual inlet ports 520 and 525, located at two corners of the blanket 500. One air flow deflector 540 and 545, is provided near each inlet port 520 and 525, respectively to aid in the even distribution of supplied air to the blanket 500.

FIG. 6 shows a blanket, generally designated by reference numeral 600, having an inlet port 620, situated along the edge of the blanket 600, similarly to the blanket 100, shown in FIG. 1. However, in this embodiment multiple airflow deflectors 640, 645 and 648, are provided to aid in the optimal air distribution within the blanket 600.

Alternatively to the blankets shown in FIGS. 4, 5 and 6, the blankets according to the present invention may include multiple inlet ports, each formed along the same or different edges of the blanket. In addition, some of the multiple inlet ports may be formed along the edge of the blanket and others at the corners of the blanket. An appropriate airflow deflector may be associated with each inlet port.

The air flow deflectors shown in FIGS. 1–6, have all been triangular is shape. However, any shape which aids in the distribution of air within the blanket may be used. FIGS. 7A, 7B, 7C, 7D and 7E, represent just some of the various shapes that may be useful. The arrows in these figures schematically represent the direction of air flow around the air flow deflector.

Figure 7A:
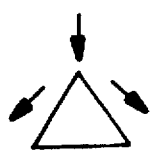
FIGS. 7A, 7B, 7C, 7D and 7E are plan views of air-flow deflectors according to various embodiments of the present invention.
Figure 7C:
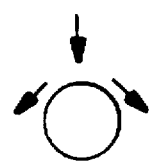
Figure 7E:
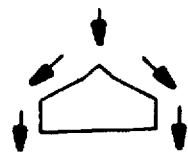
Figure 7B:
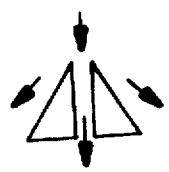
Figure 7D:
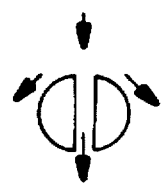

In particular, FIG. 7A shows the triangle shape described above. FIG. 7B shows a dual co-acting triangle shape. FIG. 7C describes a circular shape. FIG. 7D defines a dual co-acting half circle shape. FIG. 7E shows a polygonal shape having arcuate surfaces. As seen in the Figures, the airflow deflector can have an angular shape having a point oriented toward an inlet port of the blanket.

As noted above, the provision of airflow deflectors within the blankets according to the present invention is advantageous in promoting the free flow of air to all portions of the blanket. This can be critical in reducing the occurrence of hot or cold spots within the blanket when such is used to prevent hypothermia by supplying warm air to the blanket.

The blanket may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The blanket shown above in FIG. 1 represents a full body blanket that may be used to provide warm or cool air to the patient. However, the present invention is equally applicable to partial body blankets, such as upper body or lower body blankets. Also, the provision of airflow deflectors according to the present invention is equally useful in both adult and pediatric sized blankets.

The foregoing has been a description of certain preferred embodiments of the present invention, but is not intended to limit the invention in any way. Rather, many modifications, variations and changes in details may be made within the scope of the present invention.

What is claimed is:

1. A blanket for use with a forced air convection system, wherein said blanket includes an airflow deflector internal to said blanket, wherein said airflow deflector has a shape selected from the group consisting of an angular shape having a point oriented toward an inlet port of said blanket, a triangle, a dual co-acting triangle, a circle, a dual co-acting circle, and a polygon having arcuate surfaces, and wherein said airflow deflector is positioned adjacent the interior inlet portion of said inlet port of said blanket.

2. A blanket according to claim 1, wherein said inlet port is provided along an edge of said blanket.

3. A blanket according to claim 1, wherein said inlet port is located at a corner of said blanket.

4. A blanket according to claim 1, wherein said blanket includes two inlet ports, each having an airflow deflector associated therewith.

5. A blanket according to claim 4, wherein said inlet ports are each provided along an edge of said blanket.

6. A method of preventing hypothermia, said method comprising:

providing a blanket which may be used with a forced air convection system, wherein said blanket includes an airflow deflector internal to said blanket, wherein said airflow deflector has a shape selected from the group consisting of an angular shape having a point oriented toward an inlet port of said blanket, a triangle, a dual co-acting triangle, a circle, a dual co-acting circle, and a polygon having arcuate surfaces, and wherein said airflow deflector is positioned adjacent the interior inlet portion of said inlet port of said blanket;

connecting said blanket to a supply source of forced air; and supplying forced air from said supply source to said blanket.

* * * * *